United States Patent [19]
Shozda

[11] 4,306,094
[45] Dec. 15, 1981

[54] PREPARATION OF 4,4-DIHYDROXYDIPHENYL ETHERS

[75] Inventor: Raymond J. Shozda, Landenberg, Pa.

[73] Assignee: E. I. Du Pont de Nemours & Co., Wilmington, Del.

[21] Appl. No.: 113,239

[22] Filed: Jan. 18, 1980

[51] Int. Cl.$^3$ ............ C07C 43/00; C07C 41/00; C07C 43/20

[52] U.S. Cl. .................. 568/637; 568/635; 568/636

[58] Field of Search ............... 568/635, 636, 637

[56] References Cited

U.S. PATENT DOCUMENTS 4,153,810 5/1979 Neumann ................... 568/630

Primary Examiner—Paul J. Killos
Attorney, Agent, or Firm—S. S. Blight

[57] ABSTRACT

Substituted and unsubstituted 1,4-dihydroxybenzenes are reacted in the presence of a cation exchange resin catalyst and an inert solvent to form the corresponding 4,4'-dihydroxydiphenyl ethers.

10 Claims, No Drawings

PREPARATION OF 4,4-DIHYDROXYDIPHENYL ETHERS

BACKGROUND OF THE INVENTION

1. Field of the Invention

This invention concerns the condensation of 1,4-dihydroxybenzenes to form the corresponding 4,4'-dihydroxydiphenyl ethers.

2. Description of the Prior Art

It is known from German Specification No. 2,237,762 to prepare 4,4'-dihydroxdiphenyl ether by condensing 1,4-dihydroxybenzene in the presence of free acid-containing aluminum silicate catalyst. Of similar import is British Pat. No. 1,031,486. U.S. Pat. No. 2,739,171 concerns preparation of dihydroxy diaryl ethers in the presence of a catalyst selected from hydrofluoric and phosphoric acids, alumina, silica, zirconia and magnesia. U.S. Pat. No. 3,037,052 discloses the cation exchange resins employed in the process of this invention. Said resins are disclosed, however, for the esterification of alkyl starting reactants.

The 4,4'-dihydroxydiphenyl ethers made by the process of this invention can be reacted with dibasic carboxylic acids according to known technology to prepare polyester fibers and resins. In addition, plasticizers and antioxidants can be made by esterification or ring alkylation of the product ethers.

SUMMARY OF THE INVENTION

This invention concerns the condensation reaction of 1,4-dihydroxybenzenes to produce the corresponding 4,4'-dihydroxydiphenyl ethers. The reaction is conducted in the presence of catalyst and an inert solvent with application of heat. The reaction proceeds as follows:

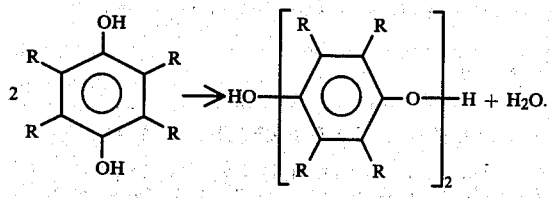

wherein R represents the same or different substituents individually selected from hydrogen, alkoxy of up to 4 carbons, alkyl of up to 6 carbons, and halogen. Preferred substituents are hydrogen and alkyl with hydrogen being most preferred.

The reaction can be carried out at atmospheric or superatmospheric pressures, it being preferred to employ pressures (up to about 5 atmospheres) moderately in excess of atmospheric pressure. Although not necessary, the use of an inert atmosphere over the reaction mixture is preferred to minimize oxidative degradation of the catalyst.

The reaction is carried out in an inert solvent or mixture of solvents comprising aromatic, alkylated aromatic, halogenated aromatic, alkyl and cycloalkyl hydrocarbons. Representative solvents are xylene, toluene, p-chlorotoluene, cumene and p-cymene. It is very important to remove water which forms during the reaction. This can be accomplished by any convenient means including azeotropic distillation.

The reaction temperature is ideally selected to achieve the optimum balance among fast reaction rate, high conversion and yield, and minimum byproduct formation. The operable range is dictated by the reactivity of the hydroxyaromatic compound, the activity of the catalyst, the stability of the reactant, product and catalyst, and the pressure. In atmospheric pressure reactions, the upper limit of temperature is set by the reflux temperature of the solvent or its water azeotrope. In closed systems, the upper temperature limit is set by the imposed pressure. The lower limit is the minimum temperature at which water is driven from the system. Generally, reaction temperatures are about 80° to 180° C., preferably about 120° to 180° C.

The cation exchange resin catalysts employed in the process of this invention are characterized by high surface area and strong acid functionality available at or near the surface. In addition, the acid functionality should be held tightly enough to withstand stirring of the reaction mass, etc., without migrating into the reaction mass. Within these guidelines, any cation exchange catalyst can be employed which is stable under reaction conditions. Preferred cation exchange catalysts are sulfonic acid resins having a surface area in excess of about 10 m$^2$/g and an ion exchange capacity in excess of about 1 meq/g.

Representative cation exchange catalysts include those sold under the names Amberlite ® and Amberlyst ®, available from Rohm and Haas; Dowex ®, available from Dow; and Nafion ®, available from Du Pont. The synthetic resin catalysts employed in the process of this invention are more uniform in their activity, have a longer useful life, are more easily regenerated, and more economical to use than acidic clay catalysts.

DETAILS OF THE INVENTION

The process of this invention is characterized by high "consumption" of hydroquinone starting reactant, high "yield" of 4,4'-dihydroxydiphenyl ether (diphenyl ether) and a low "yield" of 1,4-phenyl-4,4"-dihydroxydiphenyl ether (triphenyl ether). The terms "consumption" and "yield" are defined as follows.

$$\text{Consumption (Percent)} = \frac{\text{Starting mols} - \text{final mols of dihydroxy compound}}{\text{Starting mols}} \times 100$$

$$\text{Yield of Diphenyl Ether (Percent)} = \frac{(2) \times (\text{Mols of product})}{\text{Starting mols of dihydroxy compound} - \text{final mols of dihydroxy compound}} \times 100$$

The catalysts of this invention exhibit favorable yields of diphenyl ether of 50% or more, while maintaining yields of triphenyl ether at 15% or less. High consumption and favorable yields depend on use of the cation exchange resins defined herein with careful attention to reaction temperature. In fact, consumption and good yield have been found to be very sensitive to temperature. At the temperatures contemplated herein, employing the defined cation exchange resins, the process of this invention will consistently produce diphenyl ethers in high yields with minimal tar formation.

The following Examples illustrate the process of this invention, primary products being the diphenyl ethers:

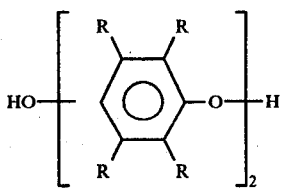

and the triphenyl ethers:

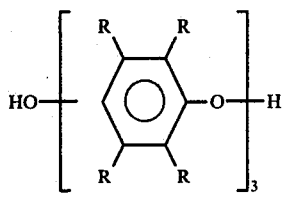

R having been defined earlier.

EXAMPLE 1

A mixture of 50 g of hydroquinone, 150 ml of xylene, and 20 g of macroreticular sulfonic acid catalyst resin made from polystyrene crosslinked with divinyl benzene (Amberlyst ® 15, Rohm and Haas) was charged to a 500 ml flask. The flask was fitted with a thermometer, a Dean-Stark trap and condenser, and a paddle stirrer operating at 300 rpm. The mixture was heated at a reflux temperature of 140° C. under a nitrogen blanket, and the water produced by the reaction was collected in the Dean-Stark trap. After three hours, the mixture was cooled and filtered. The resin was washed with diethyl ether until it was free of adhering solids. The washes were added to the filtrate and the solvents were removed under vacuum to leave 47.6 g of solid containing 14.1 g of hydroquinone, 22.6 g of diphenyl ether, and 2.0 g of triphenyl ether. The consumption was 71.8%. The yield of diphenyl ether was 68.4% and of triphenyl ether, 6.4%. The product was purified by washing out hydroquinone with warm water followed by crystallization from solvent.

EXAMPLES 2 TO 10

The general procedure of Example 1 was followed with the exceptions and results noted in Table I. The reactions were all run for 5 hours.

TABLE 1

| Example No. | Solvent | Catalyst | Reaction Temp., °C. | Consumption (%) | Yield of Diphenyl Ether (%) | Yield of Triphenyl Ether (%) | Material Balance (%) |
|---|---|---|---|---|---|---|---|
| 2 | xylene | AXN-1005[1] | 140 | 31 | 51 | 5 | 87 |
| 3 | xylene | AXN-1010[2] | 140 | 72 | 69 | 8 | 84 |
| 4 | xylene | Nafion ®[3] | 140 | 84 | 53 | 12 | 71 |
| 5 | xylene | Amberlyst ® 15 | 140 | 71 | 70 | <5 | 79 |
| 6 | cumene | Amberlyst ® 15 | 155 | 91 | 65 | 13 | 80 |
| 7 | p-chlorotoluene | Amberlyst ® 15 | 164 | 90 | 55 | 11 | 69 |
| 8 | pseudocumene | Amberlyst ® 15 | 175 | 88 | 67 | 10 | 80 |
| 9 | p-cymene | Amberlyst ® 15 | 179 | 94 | 56 | 14 | 71 |
| 10 | toluene | Amberlyst ® 15 | 112 | 19 | 69 | 3 | 95 |

Notes:
[1] Cation exchange resin similar to that designated as Amberlyst ® 15 except it has a larger surface area and a smaller cation exchange capacity.
[2] Cation exchange resin similar to AXN-1005 except it has a larger surface area.
[3] Fluorocarbon-based sulfonic acid cation exchange resin.

COMPARATIVE EXAMPLES A TO N

The procedure of Example 1 was repeated with the differences and results noted in Table 2. Example E was run for 6½ hours and Example F for 11 hours.

TABLE 2

| Comparison Letter | Solvent | Catalyst | Reaction Temp., °C. | Consumption (%) | Yield of Diphenyl Ether (%) | Yield of Triphenyl Ether (%) | Material Balance (%) |
|---|---|---|---|---|---|---|---|
| A | xylene | acid-activated clay[1] | 140 | 0 | 0 | 0 | 100 |
| B | xylene | acid-activated clay[2] | 140 | 0 | 0 | 0 | 100 |
| C | xylene | acid-activated clay[3] | 140 | 67 | 67 | 17 | 89 |
| D | xylene | acid-activated clay[4] | 140 | 84 | 53 | 20 | 78 |
| E | xylene | Amberlite ® IRC-50[5] | 140 | 0 | 0 | 0 | 90 |
| F | xylene | Dowex ® HCR-W2-H[6] | 140 | 89 | 46 | — | 52 |
| G | xylene | sulfuric acid[7] | 140 | 99 | 30 | 5 | 36 |
| H | xylene | sulfuric acid[8] | 140 | 79 | 26 | 2 | 43 |
| I | xylene | sulfuric acid[9] | 140 | 51 | 15 | 1 | 58 |
| J | xylene | ethylsulfonic acid[7] | 140 | 99 | 26 | 5 | 32 |
| K | xylene | p-toluenesulfonic acid[10] | 140 | 99+ | 22 | 4 | 30 |
| L | xylene | phosphoric acid[11] | 140 | 40 | 2 | 0 | 61 |
| M | decalin | Amberlyst ® 15 | 192 | 98 | 17 | 14 | 32 |
| N | o-dichloro- | Amberlyst ® 15 | 182 | 95 | 34 | 12 | 49 |

TABLE 2-continued

| Comparison Letter | Solvent | Catalyst | Reaction Temp., °C. | Consumption (%) | Yield of Diphenyl Ether (%) | Yield of Triphenyl Ether (%) | Material Balance (%) |
| --- | --- | --- | --- | --- | --- | --- | --- |
| | benzene | | | | | | |

Notes to Table 2:
[1] Zeolon® 100H sold by Norton Co.
[2] Zeolon® 900H sold by Norton Co.
[3] Impact® 100 sold by Milwhite Co.
[4] Impact® 150 sold by Milwhite Co.
[5] weak acid (carboxylic acid) functionalized microreticular cation exchange resin
[6] sulfonic acid microreticular (gel-type) cation exchange resin
[7] acidity is equivalent to 20 g of Amberlyst® 15 in Example 1
[8] acidity is equivalent to 4.4 g of Amberlyst® 15 in Example 1
[9] acidity is equivalent to 1.3 g of Amberlyst® 15 in Example 1
[10] acidity is equivalent to 22 g of Amberlyst® 15 in Example 1
[11] acidity is equivalent to 5.6 g of Amberlyst® 15 in Example 1.

Processes utilizing prior art catalysts such as those of Table 2 are characterized by rather heavy tar formation. On the contrary, use of the resin catalysts in the process of this invention gives high conversions and favorable yields of the diphenyl ether product. In fact, the ratio of

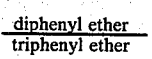

has been found to always exceed 3.3. Thus, the process of this invention produces a significant and desirable excess of diphenyl ether product relative to triphenyl ether byproduct. Furthermore, the resulting purified diphenyl ether is more homogeneous than that made by prior art processes. Since the resin catalysts lead to minimal tar formation, recycle of the solvent and the recovered hydroquinone is simplified relative to other catalysts.

The resin catalysts retain their acidity well. This is not the case with the acid-washed clays and obviously not the case for the soluble acid catalysts. The use of resin catalysts simplifies the process in that only filtration is required to remove the acid and further processing and equipment corrosion are avoided.

The resin catalysts can be easily regenerated, if necessary, and recycled. This is not so with the clays and soluble catalysts. The acid-washed clays generally retain tars tenaciously, and regeneration is consequently more difficult. Recovery and recycle of the soluble catalysts is likewise difficult and costly, and disposal requires expensive antipollution treatment.

EXAMPLE 11

Dichloro-4,4'-dihydroxydiphenyl ether

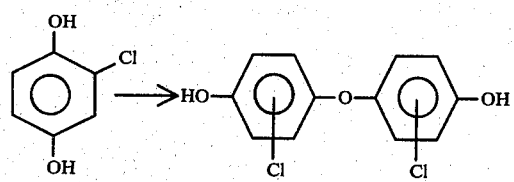

A mixture of 50 g of chlorohydroquinone, 20 g of Amberlyst® XN1010 catalyst, and 150 ml of xylene was stirred and heated for 5 hours at 144° C. Water was removed azeotropically. Workup was accomplished according to the general procedure of Example 1 to give the substituted diphenyl ether depicted above as identified by gas chromatograph and mass analysis.

EXAMPLE 12

Dimethyl-4,4'-dihydroxydiphenyl ether

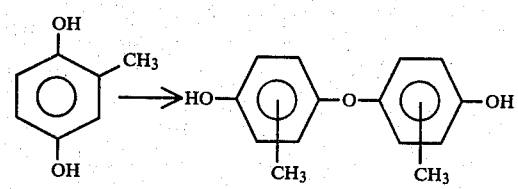

Two identical runs were made, and the products were combined. The following procedure was employed with the recited amounts representing a sum of the two runs. A mixture of 600 g of methylhydroquinone, 130 g of Amberlyst® 15 catalyst, and 2400 ml of xylene was stirred at 140° C. for 5 hours as water was removed azeotropically. The partly cooled mixture was filtered, and the collected solids were washed thoroughly with methanol. The combined filtrate/washes were freed of solvent by vacuum distillation in a rotary evaporator to leave 528 g of a viscous oil. Gas chromatographic analysis indicated the following composition: 10.3% methylhydroquinone, 69.2% dimethyl-4,4'-dihydroxydiphenyl ether, and 10.6% trimethyl-1,4-di(4-hydroxyphenoxy) benzene, (or 4-hydroxy-4'-p-hydroxyphenoxydiphenyl ether). This represents a 91% consumption of methylhydroquinone, a 72% yield of dimethyl-4,4'-dihydroxydiphenyl ether, an 11% yield of trimethyl-1,4-di(4-hydroxyphenoxy)benzene.

EXAMPLE 13

Tetramethyl 4,4'-dihydroxydiphenyl ether

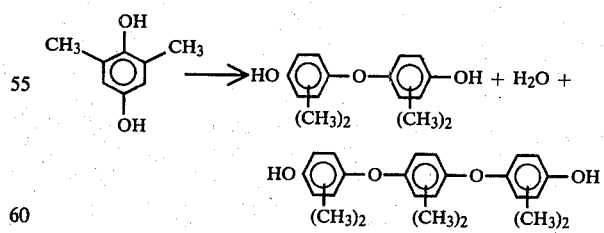

A mixture of 168 g of 2,6-dimethylhydroquinone, 121 g of Amberlyst® XN1010 catalyst, and 1200 ml of xylene was stirred and refluxed for 18 hours. Water of reaction was removed azeotropically. The mixture was cooled and filtered. The collected resin was washed with ether and the combined filtrate/washes were stripped to give 111.5 g of solid. Analysis by GC indicates the presence of 46.5 g of dimethylhydroquinone, 53.0 g of tetramethyl-4,4'-dihydroxydiphenyl ether, and 6.4 g of another component assumed to be 1-hydroxy-4-(3,5-dimethyl-4-hydroxyphenoxy)-tetramethyldiphenyl ether. Based on the dimethylhydroquinone recovered, this represents 72% consumption of the dimethylhydroquinone, an 47% yield of tetramethyl-4,4'-dihydroxydiphenyl ether, a 6% yield of the triphenyl ether.

The embodiments of the invention in which an exclusive property or privilege is claimed are defined as follows:

1. A process for producing 4,4'-dihydroxydiphenyl ether having the formula:

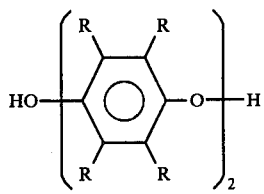

comprising condensing 1,4-dihydroxybenzenes of the formula:

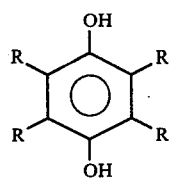

in the presence of an inert solvent and a cation exchange catalyst having a large surface area and strong acid functionality, at a temperature between about 80° to 180° C.;

wherein R represents the same or different substituents individually selected from hydrogen, alkoxy of up to 4 carbons, alkyl of up to 6 carbons, and halogen;

said process characterized by a yield of diphenyl ether of 50% or more and a yield of triphenyl ether of 15% or less.

2. A process according to claim 1 wherein the temperature is between 120° to 180° C.

3. A process according to claim 1 wherein all R substituents on the 1,4-dihydroxybenzene are H.

4. A process according to claim 1 wherein one R substituent on the 1,4-dihydroxybenzene is chlorine and the remaining R substituents are H.

5. A process according to claim 1 wherein one R substituent on the 1,4-dihydroxybenzene is methyl and the remaining R substituents are H.

6. A process according to claim 1 wherein 2 R substituents on the 1,4-dihydroxybenzene are methyl and the remaining R substituents are H.

7. A process according to claim 2 wherein all R substituents on the 1,4-dihydroxybenzene are H.

8. A process according to claim 2 wherein one R substituent on the 1,4-dihydroxybenzene is chlorine and the remaining R substituents are H.

9. A process according to claim 2 wherein one R substituent on the 1,4-dihydroxybenzene is methyl and the remaining R substituents are H.

10. A process according to claim 2 wherein 2 R substituents on the 1,4-dihydroxybenzene are methyl and the remaining R substituents are H.

* * * * *